United States Patent [19]
Bogden et al.

[11] Patent Number: 5,504,069
[45] Date of Patent: Apr. 2, 1996

[54] INHIBITION OF TRAUMA-INDUCED TUMOR GROWTH

[75] Inventors: Arthur E. Bogden, Hopedale; Jaques-Pierre Moreau, Upton, both of Mass.

[73] Assignee: Biomeasure, Inc., Milford, Mass.

[21] Appl. No.: 16,720

[22] Filed: Feb. 11, 1993

[51] Int. Cl.$^6$ ............................................ A61K 38/31
[52] U.S. Cl. ........................... 514/11; 514/14; 514/15; 514/16; 514/17
[58] Field of Search ........................... 514/16, 15, 14, 514/11, 17; 530/311; 930/160

[56] References Cited

U.S. PATENT DOCUMENTS

| | | | |
|---|---|---|---|
| 4,133,782 | 1/1979 | Vale, Jr. et al. | 530/311 |
| 4,146,612 | 3/1979 | Veber | 514/11 |
| 4,190,648 | 2/1980 | Veber | 514/11 |
| 4,211,693 | 7/1980 | Rivier et al. | 530/311 |
| 4,235,886 | 11/1980 | Freidinger et al. | 514/11 |
| 4,238,481 | 12/1980 | Rink et al. | 514/11 |
| 4,291,022 | 9/1981 | Sandrin et al. | 514/11 |
| 4,310,518 | 1/1982 | Freidinger et al. | 514/11 |
| 4,316,890 | 2/1982 | Kamber et al. | 514/11 |
| 4,328,214 | 5/1982 | Rink et al. | 514/11 |
| 4,358,439 | 11/1982 | Sieber et al. | 514/11 |
| 4,360,516 | 11/1982 | Freidinger et al. | 514/11 |
| 4,369,179 | 1/1983 | Rink et al. | 514/11 |
| 4,395,403 | 7/1983 | Bauer et al. | 514/12 |
| 4,435,385 | 3/1984 | Bauer et al. | 514/11 |
| 4,485,101 | 11/1984 | Coy et al. | 514/11 |
| 4,486,415 | 12/1984 | Freidinger | 514/11 |
| 4,522,813 | 6/1985 | Nutt | 514/11 |
| 4,585,755 | 4/1986 | Morgan et al. | 514/11 |
| 4,603,120 | 7/1986 | Kamber | 514/11 |
| 4,650,787 | 3/1987 | Schally et al. | 514/11 |
| 4,725,577 | 2/1988 | Schally et al. | 514/11 |
| 4,853,371 | 8/1989 | Coy et al. | 514/12 |
| 4,871,717 | 10/1989 | Coy et al. | 514/11 |
| 4,904,642 | 2/1990 | Coy et al. | 514/11 |

FOREIGN PATENT DOCUMENTS

| | | | |
|---|---|---|---|
| 0203031A2 | 11/1985 | European Pat. Off. | C07K 7/06 |
| 0363589A2 | 4/1990 | European Pat. Off. | C07K 7/26 |
| 0505680A1 | 9/1992 | European Pat. Off. | C07K 7/02 |
| WO89/04666 | 6/1989 | WIPO | A61K 37/24 |

OTHER PUBLICATIONS

Held, Annals New York Academy of Sciences, (1983) pp. 13–19.
Simpson–Herren et al., Cancer Treatment Reports, vol. 60, No. 12, Dec. 1976 pp. 1749–1760.
Bogden et al., "Treatment of R–3327 Prostate Tumors with a Somatostatin Analogue (Somatuline) as Adjuvant Therapy following Surgical Castration", Cancer Research 50:2646–2650, 1990.
Hurst et al., "The Therapeutic Role of Octreotide in the Management of Surgical Disorders", The American Journal of Surgery 162:499–507, 1991.
Aamdal, S., et al., Br. J. Cancer. 51:347 (1985).
Abribat, T., et al., Endocrine Society, 74th Mtg. 1384 (1992).
Alexander, Peter, et al., Adv. Exp. Med. Biol. 233:245 (1988).
Armenian, Haroutune K., et al., The Lancet, Jul. 20, 1974, p. 7873.
Brazeau, Paul, et al., Science, 179:77 (1973).
Denton, Sherwood E., et al. The Journal of Urology, 93:296 Feb. (1965).
Fisher, Bernard, et al., Cancer Research, 49:1996 (1989).
Forsberg, Karin, et al., Proc. Natl. Acad. Sci. USA, 90:393 (1993).
Hanks, Gerald E., et al., The Journal of Urology, 129:309 (1983).
Horvath, A., et al., 22nd European Peptide Symposium, Sep. 13–19, 1992, P192.
Hudson, Perry B., et al., J.A.M.A. 155:426, No. 5 (1954).
Marie, Pierre, et al., Bull. Assoc. franc p l'etude du Cancer 3:19 (1910).
McGowan, David G., J. Radiation Oncology Biol. Phys., 6:1121 (1980).
Reichlin, Seymour, N. E. J. of Medicine, 309:1495 No. 24 (1983).
Riechlin, Seymour, N. E. J. of Medicine, 309:1556 No. 25 (1983).
Schally, Andrew V., Perspectives in Cancer Research, 48:6977 (1988).
Sheldon, Curtis A., et al., The Journal of Urology, 124:626 (1980).
Simpson–Herren, Linda et al., Cancer Treatment Reports 60:1749, No. 12 (1976).
Taylor, John E., et al., Biochemical and Biophysical Research Communications, 153:81 No. 1 (1988).
Tyzzer, E. E., Journ. Med. Res. 28:309 (1913).
Van Binst, Georges, et al., Peptide Research, 5:8, No. 1 (1992).
Whitmore, Willet F., Jr., American Journal of Medicine, 2:697 (1956).
Yarden, Yosef, et al., Ann. Rev. Biochem. 57:443 (1988).

Primary Examiner—Jeffrey E. Russel
Attorney, Agent, or Firm—Fish & Richardson; William E. McGowan

[57] ABSTRACT

A method for inhibiting in a mammal the accelerated growth of a solid primary or metastatic tumor resulting from tissue trauma caused surgically, non-surgically, or by tissue ulceration, which method comprises the step of administering to the mammal a therapeutically effective amount of somatostatin or a somatostatin agonist.

20 Claims, No Drawings

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 6
        ( B ) TYPE: amino acid
        ( C ) STRANDEDNESS: Not Relevant
        ( D ) TOPOLOGY: circular ( x i ) SEQUENCE DESCRIPTION: SEQ ID NO: 1:

Pro  Phe  Trp  Lys  Thr  Phe
                                      6

( 2 ) INFORMATION FOR SEQ ID NO: 2:

( i ) SEQUENCE CHARACTERISTICS:
        ( A ) LENGTH: 6
        ( B ) TYPE: amino acid
        ( C ) STRANDEDNESS: Not Relevant
        ( D ) TOPOLOGY: circular ( i x ) FEATURE:
        ( D ) OTHER INFORMATION: Xaa is an abbreviation for 5-fluoro- trptophan.

( x i ) SEQUENCE DESCRIPTION: SEQ ID NO: 2:

Pro  Phe  Xaa  Lys  Thr  Phe
                                      6

( 2 ) INFORMATION FOR SEQ ID NO: 3:

( i ) SEQUENCE CHARACTERISTICS:

(A) LENGTH: 8
(B) TYPE: amino acid
(C) STRANDEDNESS: Not Relevant
(D) TOPOLOGY: circular (ix) FEATURE:
(D) OTHER INFORMATION: Xaa in location 4 is an abbreviation for 5-bromo-trptophan and Xaa in location 8 is an abbreviation for - aminobutyric acid.

(xi) SEQUENCE DESCRIPTION: SEQ ID NO: 3:

Asn Phe Phe Xaa Lys Thr Phe Xaa
                                8

INHIBITION OF TRAUMA-INDUCED TUMOR GROWTH

FIELD OF THE INVENTION

This invention relates to a therapeutic method for inhibiting tumor growth.

BACKGROUND OF THE INVENTION

Cytoreductive surgery has been used as adjuvant treatment for cancer patients whose tumor is believed to be too extensive for cure by either drugs or surgery alone. Accelerated growth of metastases following surgical excision or debulking of a primary tumor is a recognized clinical problem, and has been noted, in particular, in osteogenic sarcoma and testicular cancer.

The phenomenon of accelerated growth of metastases has been attributed to release of viable cells resulting from the manipulation of the tumor during surgery, or to acceleration of growth of metastases which originates before surgery on the tumor occurred. Accelerated growth of presurgical metastases has been attributed to changes in the immune status of the host secondary to removal of a major portion of the tumor or to other direct or indirect effects of the surgical procedure. It has been postulated that microscopic tumor remaining after surgery is able to grow more rapidly than is the primary tumor because the former is not subjected to factors restricting its growth, e.g., anatomical boundaries, anoxia, and nutritional deficiencies.

Enhanced growth of metastases following partial excision of implanted tumors in mice was first reported by Marie and Clunet in 1910, and by Tyzzer in 1913. These workers stated that partial removal of implanted tumors made available larger supplies of some "nutritive substances" to enhance the growth of metastases. This theory was a modification of Ehrlich's hypothesis that an actively growing tumor removed certain specific growth substances from a host animal.

More recently, Simpson-Herren et al. [Cancer Treat. Rep. 60:1749 (1976)] described a study in which a surgical procedure which was designed to simulate tumor excision but which left both the primary tumor and its spontaneous metastases undisturbed (a sham procedure) resulted in a slight increase in the thymidine index of Lewis lung tumor pulmonary metastases, and a decrease in the animals' lifespans.

Other investigators have reported similar enhanced growth of metastases as a result of surgical or non-surgical trauma or stress. Of particular note, Fisher et al. [Cancer Res. 49:1996 (1989)] evaluated the effect of removal of a primary tumor on the kinetics of cells in the metastasis of six different tumors. They found an increase in the labelling index of distant tumor focus (metastasis) associated with the removal of each of the tumor types. Serum, obtained from mice following removal of a tumor, when transferred to a mouse-recipients with the same type of tumor, resulted in an increase in the labelling index of the recipients' tumors. However, if the serum was obtained less than 18 hours after surgery, or if the mice with tumors were not subjected to surgery, then the serum failed to augment substantially the labelling index of tumors in mouserecipients. These investigators concluded that their results refute the premise that removal of a primary tumor is a local phenomenon with no biological consequences.

Alexander et al. [Adv. Exp. Med. Biol. 233:345 (1988)] studied the phenomenon of preferential growth of blood-borne cancer cells at sites of trauma, and concluded that while several factors contribute to making a wound a more favorable growth environment for metastases, a major mechanism is the release of growth factors from macrophages which have infiltrated the wound.

Adenocarcinoma of the prostate gland is a common malignancy with an incidence that rapidly rises with age after 50. It is the single most common site of cancer in males over 70. Despite advances in surgical and medical therapy for carcinoma of the prostate, this malignancy continues to be a leading cause of cancer-related death in American men. During the last 30 years, the mortality rate from prostate cancer has remained essentially unchanged.

There are a number of similarities between benign prostatic hyperplasia (BPH) and cancer. Although no casual relationship has been found between BPH and prostate cancer, there are a number of compelling similarities, including increasing incidence and prevalence with age, concordant natural history, and hormonal requirements for growth and development.

Although patients with localized disease are often asymptomatic, localized advanced disease can be accompanied by symptoms of bladder outlet obstruction requiring therapeutic surgical intervention. Benign outlet obstruction from central prostatic hypertrophy is also common, requiring transurethral resection of the prostate (TURP).

Prostatectomy for benign disease is a misnomer. Regardless of the type of prostatectomy performed for benign obstructive disease (suprapubic, retropubic, perineal or transurethral), the prostate is not removed. A variable but substantial thickness of glandular prostatic tissue remains after removal of an adenomatous enlargement of the periurethral glands. Cancer can and does develop in the remaining prostatic tissues.

Early diagnosis of carcinoma of the prostate is hindered by the lack of symptoms in men with localized tumors. Whereas most studies of prostate cancer screening have been conducted in asymptomatic men, others have dealt with screening of men before prostatectomy for presumed benign glandular involvement. Of particular importance, therefore, is that pathologic evidence of clinically occult cancer is found in 10% to 20% of men undergoing surgery for BPH. See Denton, S. E. et al. J. Urol. 93:296 (1965); Sheldon, C. A. et al. J. Urol 124:626 (1980).

Stage A carcinoma of the prostate has been defined as cancer found at autopsy incidentally and in pathologic sections of resected glands believed preoperatively to have been benign. Whitmore, W. F., Jr., Amer. J. Med. 21:697 (1956). Autopsy studies indicate that the incidence of such cases is 25% to 30% in men who were >50 years old. Hudson, P. B. et al., J.A.M.A. 155:426 (1954).

That surgical trauma may trigger these latent cancer cells into increased proliferation and/or metastasis is indicated by the following clinical examples. Armenian, et al. [Armenian, H. K. et al., Lancet 2:115–117, 1974] obtained follow-up on 611 patients up to 18 years after TURP and open prostatectomy, and found a significantly greater frequency of cancer in those with BPH (11.4%) compared with controls without BPH (3.2%). The death rate for prostate cancer was 3.7 times higher among patients with BPH than among controls. The authors also retrospectively compared 290 cancer patients with age-matched controls, and noticed a relative risk of 5.1 for prostate cancer in patients treated for BPH.

A study done by Hanks, et al. [J. Urol. U 129:309 (1983)] on 443 patients treated with radiation therapy for cancer of the prostate, compared survival of patients whose cancer was diagnosed by TURP to those diagnosed by needle biopsy, a significantly less traumatic procedure. This analysis indicated a doubling of recurrence and of deaths of patients diagnosed by TURP.

McGowan [Int. J. Radiat. Oncol. Biol. Phys. 6:1121 (1980)] reported a retrospective study of 291 patients treated with definitive radiotherapy at the Cross Cancer Institute of Edmonton. Actuarial disease-free survival and survival corrected for intercurrent death were determined for each stage and by method of diagnosis. A significant difference in 5-year disease-free survival for Stages B and C was demonstrated: 72% and 51% for needle versus TURP, respectively ($p=0.005$ by Gehan's Wilcoxon two-sided test).

The literature is replete with clinical examples illustrating the poorer prognosis and shorter survival of prostate cancer patients subjected to the more surgical trauma of TURP as compared to needle biopsy.

A surgical procedure which is gaining in popularity for the treatment of early breast cancer is "lumpectomy". Although lumpectomy is not a traumatic as mastectomy, it is a surgical procedure which does not explore, or remove, the draining lymph nodes which may contain residual cancer cells. Lumpectomy is relatively new on the surgical scene, and does not have the repertoire of clinical studies illustrating the effects of surgical trauma on tumor recurrence and survival. However, a parallelism with the prostate is likely.

Wide margin surgical excision is the first therapeutic modality applied to the treatment of primary cutaneous malignant melanoma. Depending upon the degree of local infiltration or involvement of the draining lymph nodes, surgery may be followed with radiation and/or chemotherapy. However, recurrence of tiny melanotic lesions at the surgical site or along the draining lymph channels are clinically readily recognized and a common indication of progressive disease. Because of the difficulty in treating advanced malignant melanoma, ethical considerations have not permitted clinical studies comparing survival or metastatic spread of cutaneous malignant melanoma in patients subjected or not subjected to surgical excision of the primary cutaneous lesion.

It has recently been reported that a somatostatin analog inhibits growth but not wound healing. See Abribat T. et al. Endocrine Society, 74th Annual Meeting, Abstract #1384 (1992).

SUMMARY OF THE INVENTION

The present invention relates to a therapeutic method for inhibiting in a mammal the accelerated growth of a solid primary or metastatic tumor resulting from tissue trauma caused surgically, non-surgically, or by tissue ulceration. The method includes the step of administering to said mammal a therapeutically effective amount of somatostatin or a somatostatin agonist.

Definition of "somatostatin agonist" will be provided below. A therapeutically effective amount depends upon the condition being treated, the route of administration chosen, and the specific activity of the compound used, and ultimately will be decided by the attending physician or veterinarian.

The tumors which can be treated by this method include, but are not limited to, epithelial tumors (tumors of epithelial tissues) such as prostate tumor, breast tumor, colon tumor, lung tumor, and melanoma. Preferably, the administering step is performed by topical or subcutaneous application to the site of the trauma.

Other features and advantages of the invention will be apparent from the following description of the preferred embodiments thereof, and from the claims.

Abbreviations
β-Nal=β-naphthylalanine
β-Pal=β-pyridylalanine
hArg(Bu)=N-guanidino-(butyl)-homoarginine
hArg(Et)$_2$=N, N'-guanidino-(dimethyl)-homoarginine
hArg(CH$_2$CF$_3$)$_2$=N, N'-guanidino-bis-(2,2,2,-trifluoroethyl-)homoarginine
hArg(CH$_3$, hexyl)=N, N'-guanidino-(methyl, hexyl)homoarginine
Lys(Me)=N$^\epsilon$-methyllysine
Lys(iPr)=N$^\epsilon$-isopropyllysine
AmPhe=aminomethylphenylalanine
AChxAla=aminocyclohexylalanine
Abu=α-aminobutyric acid
Tpo=4-thiaproline
MeLeu=N-methylleucine
Orn=ornithine
Nle=norleucine
Nva=norvaline
Trp(Br)=5-bromo-tryptophan
Trp(F)=5-fluoro-tryptophan
Trp(NO$_2$)=5-nitro-tryptophan
Gaba=γ-aminobutyric acid
Bmp=β-mercaptopropionyl
Ac=acetyl

DESCRIPTION OF THE PREFERRED EMBODIMENTS

Somatostatin and its agonists

Somatostatin (somatotropin release inhibiting factor, or SRIF) is an inhibitor of secretion of the growth hormone and was originally isolated from the hypothalamus. Brazeau et al. Science 179:77 (1973). Somatostatin has a broad spectrum of biological effects, participates in a high number of biological processes and in the majority of cases, plays a role of an inhibitory factor. E.g., it inhibits the release of prolactin, insulin, glucagon, gastrin, secretin, and cholecystokinin. Reichlin, S. Somatostatin, N. Eng. J. Med. 309:1495 and 1556 (1983).

One of the most important effects of somatostatin as growth-inhibiting factor consists in its capability to influence various forms of pathological cell growth. It is well known from the literature that it exerts an inhibitory action on the growth of cancerous cells. See Schally, A. V. Cancer Res. 48:6988 (1988); and Taylor et al. Biochem. Biophys. Res. Commun. 153:81 (1988).

Likely, somatostatin antagonizes the effect of some growth factors on tumor proliferation. It has been shown recently that somatostatin and some somatostatin analogs are capable of activating the tyrosine phosphatase enzyme which antagonizes the effect of tyrosine kinases, a mediator on the mitotic effect of growth factors (e.g., epidermal growth factor, insulin-like growth factor, etc.). Schally, A. V. Cancer Res. 48:6977 (1988); Yarden, et al. Ann. Rev. Biochem. 57:443 (1989).

Native somatostatin has a very short duration of effect in vivo since it is rapidly inactivated by endo- and exopeptidase. Many novel analogs have been prepared in order to enhance the duration of effect, biological activity and selectivity of this hormone. Such analogs will be called somatostatin agonists herein.

Somatostatin agonists which can be used to practice the therapeutic method of the present invention include, but are not limited to, those covered by formulas or those specifically recited in the publications set forth below, all of which are hereby incorporated by reference.

EP Application No. 0 505 680 A1 (Inventor: G. Keri);
Van Binst, G. et al. Peptide Research 5:8 (1992);
Horvath, A. et al. Abstract, "Conformations of Somatostatin Analogs Having Antitumor Activity", 22nd European peptide Symposium, Sep. 13–19, 1992, Interlaken, Switzerland;
EP Application 0 363 589 A2 (1990);
U.S. Pat. No. 4,904,642 (1990);
U.S. Pat. No. 4,871,717 (1989);
U.S. Pat. No. 4,853,371 (1989);
U.S. Pat. No. 4,725,577 (1988);
U.S. Pat. No. 4,650,787 (1987);
U.S. Pat. No. 4,603,120 (1986);
U.S. Pat. No. 4,585,755 (1986);
EP Application 0 203 031 A2 (1986);
U.S. Pat. No. 4,522,813 (1985);
U.S. Pat. No. 4,486,415 (1984);
U.S. Pat. No. 4,485,101 (1984);
U.S. Pat. No. 4,435,385 (1984);
U.S. Pat. No. 4,395,403 (1983);
U.S. Pat. No. 4,369,179 (1983);
U.S. Pat. No. 4,360,516 (1982);
U.S. Pat. No. 4,358,439 (1982);
U.S. Pat. No. 4,328,214 (1982);
U.S. Pat. No. 4,316,890 (1982);
U.S. Pat. No. 4,310,518 (1982);
U.S. Pat. No. 4,291,022 (1981);
U.S. Pat. No. 4,238,481 (1980);
U.S. Pat. No. 4,235,886 (1980);
U.S. Pat. No. 4,211,693 (1980);
U.S. Pat. No. 4,190,648 (1980);
U.S. Pat. No. 4,146,612 (1979); and
U.S. Pat. No. 4,133,782 (1979).

Preferred somatostatin agonists include, but are not limited to, the following somatostatin analogs which are disclosed in the above-cited references:

H-D-Phe-Cys-Phe-D-Trp-Lys-Thr-Cys-Thr-OH;
H-D-phe-Cys-Phe-D-Trp-Lys-Thr-Cys-Thr-$NH_2$;
H-D-Trp-Cys-Tyr-D-Trp-Lys-Val-Cys-Thr-$NH_2$;
H-D-Trp-Cys-Phe-D-Trp-Lys-Thr-Cys-Thr-$NH_2$;
H-D-Phe-Cys-Tyr-D-Trp-Lys-Val-CYs-Thr-$NH_2$;
H-D-Phe-Cys-Tyr-D-Trp-Lys-Val-Cys-Trp-$NH_2$;
H-D-phe-Cys-Tyr-D-Trp-Lys-Val-Cys-Thr-$NH_2$;
Ac-D-phe-Lys*-Tyr-D-Trp-Lys-Val-Asp-Thr-$NH_2$ (an amide bridge formed between Lys* and Asp);
Ac-hArg($Et$)$_2$-Gly-Cys-Phe-D-TrP-LYs-Thr-CYs-$NH_2$;
Ac-D-hArg($Et$)$_2$-Gly-Cys-Phe-D-Trp-Lys-Thr-Cys-Thr-$NH_2$;
Ac-D-hArg(Bu)-Gly-Cys-Phe-D-Trp-Lys-Thr-Cys-Thr-$NH_2$;
Ac-D-hArg($Et$)$_2$-Cys-Phe-D-Trp-Lys-Thr-Cys-Thr-$NH_2$;
Ac-L-hArg($Et,_2$-Cys-phe-D-Trp-Lys-Thr-Cys-Thr-$NH_2$;
Ac-D-hArg($CH_2CF_3$)$_2$-Cys-Phe-D-TrP-LYs-Thr-CYs-Thr-$NH_2$;
Ac-D-hArg($CH_2CF_3$)$_2$-Gly-Cys-Phe-D-TrP-LYs-Thr-CYs-Thr-$NH_2$;
Ac-D-hArg ($CH_2CF_3$)$_2$-Gly-Cys-Phe-D-Trp-Lys-Thr-Cys-Phe-$NH_2$;
Ac-D-hArg($CH_2CF_3$)$_2$-Gly-Cys-Phe-D-TrP-LYs-Thr-CYs-Thr-NHEt
Ac-L-hArg($CH_2$-$CF_3$)$_2$-Gly-Cys-Phe-D-Trp-Lys-Thr-Cys-Thr-$NH_2$
Ac-D-hArg($CH_2CF_3$)$_2$-Gly-Cys-Phe-D-Trp-Lys(Me)-Thr-Cys-Thr-$NH_2$
Ac-D-hArg($CH_2CF_3$)$_2$-Gly-Cys-Phe-D-Trp-Lys(Me)-Thr-Cys-Thr-NHEt
Ac-hArg($CH_3$, hexyl)-Gly-Cys-Phe-D-Trp-Lys-Thr-Cys-Thr-$NH_2$
H-hArg(hexyl$_2$)-Gly-Cys-Phe-D-Trp-Lys-Thr-Cys-Thr-$NH_2$;
Ac-D-hArg($Et$)$_2$-Gly-Cys-Phe-D-Trp-Lys-Thr-Cys-Thr-NHEt;
Ac-D-hArg($Et$)$_2$-Gly-Cys-Phe-D-Trp-Lys-Thr-Cys-Phe-$NH_2$;
Propionyl-D-hArg($Et$)$_2$-Gly-Cys-Phe-D-Trp-Lys(iPr)-Thr-Cys-Thr-$NH_2$;
Ac-D-β-Nal-Gly-Cys-Phe-D-Trp-Lys-Thr-Cys-Gly-hArg($Et$)$_2$-$NH_2$;
Ac-D-Lys(iPr)-Gly-Cys-Phe-D-Trp-Lys-Thr-Cys-Thr-$NH_2$;
Ac-D-hArg($CH_2CF_3$)$_2$-D-hArg($CH_2CF_3$)$_2$-Gly-Cys-Phe-D-Trp-Lys-thr-Cys-Thr-$NH_2$;
Ac-D-hArg($CH_2CF_3$)$_2$-D-hArg($CH_2CF_3$)$_b$ $_2$-Gly-Cys-Phe-D-Trp-Lys-Thr-Cys-Phe-$NH_2$;
Ac-D-hArg($Et$)$_2$-D-hArg($Et$)$_2$-Gly-Cys-Phe-DTrp-Lys-Thr-Cys-Thr-$NH_2$;
Ac-Cys-Lys-Asn-4-Cl-Phe-Phe-D-Trp-Lys-Thr-Phe-Thr-Ser-D-Cys-$NH_2$;
Bmp-Tyr-D-Trp-Lys-Val-Cys-Thr-$NH_2$;
Bmp-Tyr-D-Trp-Lys-Val-Cys-Phe-$NH_2$;
Bmp-Tyr-D-Trp-Lys-Val-Cys-p-Cl-Phe-$NH_2$;
Bmp-Tyr-D-Trp-Lys-Val-Cys-β-Nal-$NH_2$
H-D-β-Nal-Cys-Tyr-D-Trp-Lys-Val-Cys-Thr-$NH_2$;
H-D-Phe-Cys-Tyr-D-Trp-Lys-Abu-Cys-Thr-$NH_2$;
H-D-Phe-Cys-Tyr-D-Trp-Lys-Abu-Cys-β-Nal-$NH_2$;
H-pentafluoro-D-Phe-Cys-Tyr-D-Trp-Lys-Val-Cys-Thr-$NH_2$;
Ac-D-β-Nal-Cys-pentafluoro-Phe-D-Trp-Lys-Val-Cys-Thr-$NH_2$;
H-D-β-Nal-Cys-Tyr-D-Trp-Lys-Val-Cys-β-Nal-$NH_2$;
H-D-Phe-Cys-Tyr-D-Trp-Lys-Val-Cys-β-Nal-$NH_2$;
H-D-β-Nal-Cys-Tyr-D-Trp-Lys-Abu-Cys-Thr-$NH_2$;
H-D-p-Cl-Phe-Cys-Tyr-D-Trp-Lys-Abu-Cys-Thr-$NH_2$;
Ac-D-p-Cl-Phe-Cys-Tyr-D-Trp-Lys-Abu-Cys-Thr-$NH_2$;
H-D-phe-Cys-β-Nal-D-Trp-Lys-Val-Cys-Thr-$NH_2$;
H-D-Phe-Cys-Tyr-D-Trp-Lys-Cys-Thr-$NH_2$;
cyclo (Pro-Phe-D-Trp-N-Me-Lys-Thr-Phe);
cyclo (Pro-Phe-D-Trp-N-Me-Lys-Thr-Phe);
cyclo (Pro-Phe-D-Trp-Lys-Thr-N-Me-Phe);
cyclo (N-Me-Ala-Tyr-D-Trp-Lys-Thr-Phe);
cyclo (Pro-Tyr-D-Trp-Lys-Thr-Phe);
cyclo (Pro-Phe-D-Trp-Lys-Thr-Phe);
cyclo (Pro-Phe-L-Trp-Lys-Thr-Phe) (SEQ ID NO): 1);
cyclo (Pro-Phe-D-Trp (F)-Lys-Thr-Phe;
cyclo (Pro-Phe-Trp (F)-Lys-Thr-Phe) (SEQ ID NO: 2);
cyclo (Pro-Phe-D-Trp-Lys-Ser-Phe);
cyclo (Pro-Phe-D-Trp-Lys-Thr-p-Cl-Phe);

cyclo (D-Ala-N-Me-D-Phe-D-Thr-D-Lys-Trp-D-Phe);
cyclo (D-Ala-N-Me-D-Phe-D-Val-Lys-D-Trp-D-Phe);
cyclo (D-Ala-N-Me-D-Phe-D-Thr-Lys-D-Trp-D-Phe);
cyclo (D-Abu-N-Me-D-Phe-D-Val-Lys-D-Trp-D-Tyr);
cyclo (Pro-Tyr-D-Trp-t-4-AchxAla-Thr-Phe);
cyclo (Pro-Phe-D-Trp-t-4-AchxAla-Thr-Phe);
cyclo (N-Me-Ala-Tyr-D-Trp-Lys-Val-Phe);
cyclo (N-Me-Ala-Tyr-D-Trp-t-4-AchxAla-Thr-Phe);
cyclo (Pro-Tyr-D-Trp-4-Amphe-Thr-Phe);
cyclo (Pro-Phe-D-Trp-4-Amphe-Thr-Phe);
cyclo (N-Me-Ala-Tyr-D-Trp-4-Amphe-Thr-Phe);
cyclo (Asn-Phe-Phe-D-Trp-Lys-Thr-Phe-Gaba);
cyclo (Asn-Phe-Phe-D-Trp-Lys-Thr-Phe-Gaba-Gaba);
cyclo (Asn-Phe-D-Trp-Lys-Thr-Phe);
cyclo (Asn-Phe-Phe-D-Trp-Lys-Thr-Phe-NH(CH$_2$)$_4$CO);
cyclo (Asn-Phe-Phe-D-Trp-Lys-Thr-Phe-β-Ala);
cyclo (Asn-Phe-Phe-D-Trp-Lys-Thr-Phe-D-Glu)-OH;
cyclo (Phe-Phe-D-Trp-Lys-Thr-Phe);
cyclo (Phe-Phe-D-Trp-Lys-Thr-Phe-Gly);
cyclo (Phe-Phe-D-Trp-Lys-Thr-Phe-Gaba);
cyclo (Asn-Phe-Phe-D-Trp-Lys-Thr-Phe-Gly);
cyclo (Asn-Phe-Phe-D-Trp (F)-Lys-Thr-Phe-Gaba);
cyclo (Asn-Phe-Phe-D-Trp (NO$_2$)-Lys-Thr-Phe-Gaba);
cyclo (Asn-Phe-Phe-Trp(Br)-Lys-Thr-Phe-Gaba) (SEQ ID NO: 3);
cyclo (Asn-Phe-Phe-D-Trp-Lys-Thr-Phe(I)-Gaba);
cyclo (Asn-Phe-Phe-D-Trp-Lys-Thr-Tyr(But)-Gaba);
cyclo (Bmp-Lys-Asn-Phe-Phe-D-Trp-Lys-Thr-Phe-Thr-Pro-Cys)-OH;
cyclo (Bmp-Lys-Asn-Phe-Phe-D-Trp-Lys-Thr-Phe-Thr-Pro-Cys)-OH;
cyclo (Bmp-Lys-Asn-Phe-Phe-D-Trp-Lys-Thr-Phe-Thr-Tpo-Cys)-OH;
cyclo (Bmp-Lys-Asn-Phe-Phe-D-Trp-Lys-Thr-phe-Thr-MeLeu-Cys)-OH;
cyclo (Phe-Phe-D-Trp-Lys-Thr-Phe-Phe-Gaba);
cyclo (Phe-Phe-D-Trp-Lys-Thr-Phe-D-Phe-Gaba);
cyclo (Phe-Phe-D-Trp(5F)-Lys-Thr-Phe-Phe-Gaba);
cyclo (Asn-Phe-Phe-D-Trp-Lys(Ac)-Thr-Phe-NH—(CH$_2$)$_3$—CO);
cyclo (Lys-Phe-Phe-D-Trp-Lys-Thr-Phe-Gaba);
cyclo (Lys-Phe-Phe-D-Trp-Lys-Thr-Phe-Gaba); and
cyclo (Orn-Phe-Phe-D-Trp-Lys-Thr-Phe-Gaba).

Note that for all somatostatin agonists described herein, each amino acid residue represents the structure of NH—C(R)H—CO—, in which R is the side chain. Lines between amino acid residues represent peptide bonds which join the amino acids. Also, where the amino acid residue is optically active, it is the L-form configuration that is intended unless D-form is expressly designated. A disulfide bridge is formed between two Cys residues; however, it is not shown.

Also preferred somatostatin agonists of the invention is of the following formula:

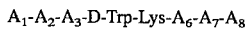

wherein

A$_1$ is a D- or L-isomer of β-Nal, Trp, β-Pal, Phe, substituted Phe, or deleted; A$_2$ and A7, independently, is Cys, Asp, or Lys, and are covalently linked either via a disulfide bridge or an amide bridge; A$_3$ is Phe or o-, m- or p-substituted X-Phe where X is a halogen, OH, NH$_2$, NO$_2$ or C$_{1-3}$ alkyl; A$_6$ is Val, Thr, Ser, Ala, Phe, β-Nal, Abu, Ile, Nle, or Nva; and A$_8$ is Phe, Tyr, Trp, Ser, β-Nal, or deleted; providing that when one of A$_2$ and A$_7$ is Cys, the other is also Cys, and that when neither of A$_2$ and A$_7$ is Cys, A$_2$ is different from A$_7$.

Use of linear somatostatin agonists of the following formula is also within the invention:

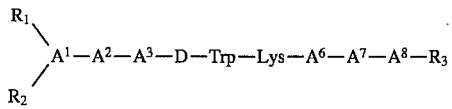

wherein

A$^1$ is a D- or L- isomer of Ala, Leu, Ile, Val, Nle, Thr, Ser, β-Nal, β-Pal, Trp, Phe, 2,4-dichloro-Phe, pentafluoro-Phe, p-X-Phe, or o-X-Phe, wherein X is CH$_3$, Cl, Br, F, OH, OCH$_3$ or NO$_2$;

A$^2$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is CH$_3$, Cl, Br, F, OH, OCH$_3$ or NO$_2$;

A$^3$ is pyridyl-Ala, Trp, Phe, β-Nal, 2,4-dichloro-Phe, pentafluoro-Phe, o-X-Phe, or p-X-Phe, wherein X is CH$_3$, Cl, Br, F, OH, OCH$_3$ or NO$_2$;

A$^6$ is Val, Ala, Leu, Ile, Nle, Thr, Abu, or Ser;

A$^7$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is CH$_3$, Cl, Br, F, OH, OCH$_3$ or NO$_2$;

A$^8$ is a D- or L-isomer of Ala, Leu, Ile, Val, Nle, Thr, Ser, Phe, β-Nal, pyridyl-Ala, Trp, 2,4-dichloro-Phe, pentafluoro-Phe, p-X-Phe, or o-X-Phe, wherein X is CH$_3$, Cl, Br, F, OH, OCH$_3$ or NO$_2$;

each $R_1$ and $R_2$, independently, is H, lower acyl or lower alkyl; and $R_3$ is OH or NH$_2$; provided that at least one of A$^1$ and A$^8$ and one of A$^2$ and A$^7$ must be an aromatic amino acid; and further provided that A$^1$, A$^2$, A$^7$ and A$^8$ cannot all be aromatic amino acids.

Particularly preferred linear agonists to be used in the method of this invention include:

H-D-Phe-p-chloro-Phe-Tyr-D-Trp-Lys-Thr-Phe-Thr-NH$_2$.

H-D-Phe-p-NO$_2$-Phe-Tyr-D-Trp-Lys-Val-Phe-Thr-NH$_2$;

H-D-Nal-p-chloro-Phe-Tyr-D-Trp-Lys-Val-Phe-Thr-NH$_2$.

H-D-phe-Phe-Phe-D-Trp-Lys-Thr-Phe-Thr-NH$_2$.

H-D-phe-phe-Tyr-D-Trp-Lys-Val-Phe-Thr-NH$_2$.

H-D-Phe-p-chloro-Phe-Tyr-D-Trp-Lys-Val-Phe-Thr-NH$_2$.

H-D-Phe-Ala-Tyr-D-Trp-Lys-Val-Ala-β-D-Nal-NH$_2$

If desired, a hydrophobic moiety (e.g., an acyl group) can be attached to the nitrogen of the amino group at the N terminus of a somatostatin agonist.

Proliferation of tumor following trauma

Before disclosing preferred methods of using somatostatin or its agonist to inhibit in a mammal the accelerated growth of a solid primary or metastatic tumor resulting from tissue trauma caused surgically, nonsurgically, or by tissue ulceration, experimental evidence of the trauma-induced tumor growth is first provided.

The proliferative surge of residual tumor in surgically treated animals would indicate the release of growth factors from the trauma area. To determine duration of the release of such factors post trauma, surgical trauma was induced in five groups (10 animals per group), and five groups (10 animals per group) were retained as nonsurgically treated controls. Treatment of the various groups is summarized in Table 1.

TABLE 1

Trauma Induced Proliferation of Subcutaneous Melanoma

| Group No. | Treatment | Day Post Implantation | Tumor Weight | Growth Rate |
|---|---|---|---|---|
| 1 | Surgery left flank, day 0. Tumor implanted s.c., right flank, day 0. | 14 | 1031 ± 112 | 73.6 |
| 2 | Surgery left flank, day 0. Tumor implanted s.c., right flank, day 1. | 15 | 1391 ± 166 | 92.7 |
| 3 | Surgery left flank, day 0. Tumor implanted s.c., right flank, day 2. | 14 | 1333 ± 244 | 95.2 |
| 4 | Surgery left flank, day 0. Tumor implanted s.c., right flank, day 3 | 15 | 764 ± 166 | 50.9 |
| 5 | Surgery left flank, day 0. Tumor implanted s.c., right Rank, day 4. | 14 | 558 ± 200 | 39.8 |
| 6 | No surgery control. Tumor implanted s.c., right flank, day 0. | 14 | 454 ± 76 | 32.5 |
| 7 | No surgery control. Tumor implanted s.c., right flank, day 1. | 15 | 972 ± 232 | 64.8 |
| 8 | No surgery control. Tumor implanted s.c., right flank, day 2. | 14 | 813 ± 268 | 58.1 |
| 9 | No surgery control. Tumor implanted s.c., right flank, day S. | 15 | 950 ± 185 | 63.3 |
| 10 | No surgery control. Tumor implanted s.c., right flank, day 4. | 14 | 448 ± 111 | 31.9 |

Surgical Procedure: Sterile excision of a full thickness skin graft from the left flank. Wound edges immediately approximated and closed with Michel clamps. Surgically treated animals were carefully randomized.
B16 Melanoma: Implant $10^5$ B16-F10 cells, s.c., right flank in p.m.
The units of tumor weight and growth rate are mg and mg/day, respectively.

Tumor sizes were determined three times weekly with Vernier calipers, and the growth rate per day was calculated at the end of the test. period. In Table 1, comparisons are made between Group 1 and Group 6; Group 2 and Group 7; Group 3 and Group 8; Group 4 and Group 9; and Group 5 and Group 10. The percent increase in the growth rate per day in the surgically treated groups over that of the corresponding non-traumatized control indicates that the stimulus to tumor growth begins to occur on the day of traumatization. The resultant effect on tumor growth is easily measurable thereafter, and declines to normal growth levels by day 4.

These results correlate very closely with the observations by Aamdal, et al. [Br. J. Cancer 51:347 (1985)], who measured the mitotic activity of human tumor xenografts implanted subrenal capsule in mice. In his studies, human melanomas, colon carcinomas and sarcomas exhibited a proliferative surge following the surgical trauma of subrenal capsule implantation, Inhibition of trauma-induced growth of prostate tumor The following study was designed to demonstrate the therapeutic effect of applying BIM-23014 (a somatostatin agonist with the structure of H-D-β-Nal-Cys-Tyr-D-Trp-Lys-Val-Cys-Thr-NH$_2$), topically, either to the tumor site or to the surgically traumatized site, for inhibiting the proliferative surge of prostate tumor following surgical trauma. The results, as well as a brief description of the experiment, are presented in Table 2 below. Data are reported as means ±s.e.m. on 10 animals/group.

TABLE 2

Treatment of Surgical Trauma-Induced Proliferation (Prostate Tumor)

| Group No. | Treatment | Change in Tumor Weight Day 6–17 (mgs) | Percent Test/ Control |
|---|---|---|---|
| 1 | Tumor implanted s.c., right flank, day 0. No surgery. Shelf control. | 1921 ± 260 | 123 |
| 2 | Tumor implanted s.c., right flank, day 0. Surgery left flank, day 3. Shelf control. | 2366 ± 434 | |
| 3 | Tumor implanted s.c., right flank, day 0. Surgery left flank, day 3. 10% DMSO/ saline vehicle, topical to tumor, b.i.d., q.d. 3(p.m.). | 2100 ± 321 | 98 |
| 4 | Tumor implanted s.c., right flank, day 0. Surgery left flank, day 3. BIM-23014 topical to tumor, b.i.d., q.d. 3(p.m.). | 2052 ± 196 | |
| 5 | Tumor implanted s.c., right flank, day 0. Surgery left flank, day 3. 10% DMSO/ saline vehicle, topical to surgery area, b.i.d., q.d. 3(p.m.). | 2410 ± 289 | 77 |
| 6 | Tumor implanted s.c., right flank, day 0. Surgery left flank, day 3. BIM-23014, topical to surgery area, b.i.d., q.d. 3(p.m.). | 1854 ± 328 | |

More specifically, tumor implantation was performed on all test animals, i.e., Groups 1–6, by implanting subcutaneously a 2 mm$^3$ mince of 2PR121D(1), a prostate tumor cell line, in the right flank on day 0. Surgical trauma was induced in the left flank of five groups of Noble male rats, i.e., Groups 2–6. The surgical procedure was carried out by first excising under sterile precautions a full thickness skin graft from the left flank. A 15 mmD test tube marker was used to outline the skin to be excised for standardizing the surgical area. The wound edges were immediately approximated and closed with Michel clamps. The surgery was performed on day 3 following implantation of prostate tumor cells.

Both placebo (10% dimethyl sulfoxide ["DMSO"] in saline) and BIM-23014 (10 mg/ml in 10% DMSO/saline vehicle) were applied topically with gentle rubbing for a duration of exactly one minute, volume applied being 0.1 ml.

As shown in Table 2, prostate tumor cells implanted s.c. in non-surgically traumatized animals on day 0 produced tumors with a mean weight of 1921 mgs between day 6–17 (Group 1). The same size inoculum of prostate tumor cells, implanted opposite to the traumatized area, produced tumors weighing 2366 mgs in the same time period (Group 2). Thus, surgical trauma did induce accelerated proliferation of prostate tumor as indicated by the Test/Control value of 123%. BIM-23014 applied directly to the tumor site resulted in tumors weighing 2052 mgs (Group 4); whereas the 10% DMSO/saline placebo applied directly to the tumor site resulted in tumors weighing 2100 mgs (Group 3), producing a Test/Control value of only 98%.

When the 10% DMSO/saline vehicle was applied to the surgically traumatized area on the left flank (Group 5), there was no apparent effect with the tumors on the right flank growing to an average of 2410 mgs (cf. 2366 mgs for Group 2). Importantly, when BIM-23014 was applied topically to the surgically traumatized area (left flank) rather than to the non-traumatized area (right flank) (Group 6), tumor growth was markedly inhibited resulting in tumors weighing mgs, a Test/Control value of 77%.

In another study, a fine mince of 11095 rat prostate tumor tissue, 1–2 mm$^3$, was implanted s.c., right flank, in Fischer 344 strain rats on day 0. On day 2, 48 hours later, all animals were surgically traumatized by excising a 1 cm$^2$ full dermal thickness graft from the opposite (left) flank. Topical application of the 40% DMSO/saline vehicle, or BIM-23014, to the surgical site was initiated in the p.m. of day 2 and continued b.i.d. to day 9. Tumor sizes were determined with Vernier calipers and weight calculated from the formula for an ellipsoid length ×width$^2$/2 (mg). As shown in Table 3 application of BIM-23014 resulted in a test/control value of 48% (Group 3/Group 1).

TABLE 3

Suppression of the Proliferative Surge Following Surgical Trauma (11095 Prostate Tumor)

| Group No. | Treatment | Tumor Weight* (mg) Day 9 | Percent Test/ Control |
|---|---|---|---|
| 1 | Surgery Day 2, untreated shelf control. | 1973 ± 312 | — |
| 2 | Surgery Day 2, 40% DMSO/saline to surgical area, b.i.d., q.d. 2–9. | 1132 ± 62 | 57 |
| 3 | Surgery Day 2, BIM-23014 in 40% DMSO/saline to surgical area, b.i.d., q.d. 2–9. | 967 ± 135 | 48 |

*Data presented as means s.e.m. on 6 to 10 animals/group. Significance of difference: Group 1 and Group 2 = p < 0.001; Group 1 and Group 3 = p < 0.001.

Inhibition of trauma-induced growth of breast tumor

The response of human breast tumor xenografts to surgical trauma resulting from a tumor debulking procedure (cytoreduction) is demonstrated by an experiment in which athymic nude female mice were used as xenograft recipients of the undifferentiated human breast tumor cells, MX-1. One group of mice were implanted bilaterally with MX-1 cells; whereas another group of animals were implanted only on the right flank on day 0. On day 13, the left flank tumors on the first group mice were surgically excised. The results show that tumors in animals subjected to a cytoreductive (lumpectomy) procedure experienced an increase in the growth rate over that of the non-surgically traumatized animals, i.e., the change in tumor size (weight) during the 10 day period post surgery being 747 mgs vs 618 mgs.

The following study was designed to demonstrate the therapeutic effect of applying BIM-23014 topically, either to the tumor site or to the surgically traumatized site, for inhibiting the proliferative surge of breast tumor following surgical trauma. The results, as well as a brief description of the experiment, are presented in Table 4 below. Data are reported as means ±s.e.m. on 8 animals/group.

TABLE 4

Treatment of Surgical Trauma-Induced Proliferation (Human Breast Tumor)

| Group No. | Treatment | Tumor Weight (mg) Day 14 | Percent Test/ Control |
|---|---|---|---|
| 1 | Tumor implanted s.c., right flank, day 0. No surgery. Shelf control. | 245 ± 40 | 135 |
| 2 | Tumor implanted s.c., right flank, day 0. Surgery left flank, day 3. Shelf control. | 332 ± 46 | |
| 3 | Tumor implanted s.c., right flank, day 0. Surgery left flank day 3. 10% DMSO/saline vehicle, topical to tumor, b.i.d., q.d. 3 (p.m.). | 339 ± 63 | 147 |
| 4 | Tumor implanted s.c., right flank, day 0. Surgery left flank, day 3. BIM-23014, topical to tumor, b.i.d., q.d. 3 (p.m.). | 500 ± 116 | |
| 5 | Tumor implanted s.c., right flank, day 0. Surgery left flank, day 3. 10% DMSO/saline vehicle, topical to surgery area, b.i.d., q.d. 3 (p.m.). | 408 ± 159 | 72 |
| 6 | Tumor implanted s.c., right flank, day 0. Surgery left flank, day 3. BIM-23014, topical to surgery area, b.i.d., q.d. 3 (p.m.). | 296 ± 52 | |

More specifically, tumor implantation was performed on all test animals, i.e., Groups 1–6, by implanting subcutaneously a 2 mm$^3$ mince of MX-1 cells in the right flank on day 0. Surgical trauma was induced in the left flank of five groups of athymic nude female mice, i.e., Groups 2–6. A 15 mmD test tube marker was used to outline the skin to be excised for standardizing the surgical area. The surgical procedure was carried out by first excising under sterile precautions a full thickness skin graft from the left flank. The wound edges were immediately approximated and closed with Michel clamps. The surgery was performed on day 3 following implantation of MX-1 cells.

Both placebo (10% DMSO in saline) and BIM-23014 (10 mg/ml in 10% DMSO/saline vehicle) were applied topically with gentle rubbing for a duration of exactly one minute, volume applied being 0.05 ml (1 drop).

As shown in Table 4, breast tumor cells implanted s.c. in non-surgically traumatized animals on day 0 produced tumors with a mean weight of 245 mgs on day 14 (Group 1). The same size inoculum of breast tumor cells, implanted opposite to the traumatized area, produced tumors weighing 332 mgs in the same time period (Group 2). Thus, surgical trauma did induce accelerated proliferation of breast tumor as indicated by the Test/Control value of 135%. BIM-23014 applied directly to the tumor site resulted in tumors weighing 500 mgs (Group 4); whereas the 10% DMSO/saline placebo applied directly to the tumor site resulted in tumors weighing 339 mgs (Group 3), producing a Test/Control value of 147%.

When the 10% DMSO/saline vehicle was applied to the surgically traumatized area on the left flank of animals bearing a tumor in the non-traumatized right flank (Group 5), there was no inhibitory effect with the tumors growing to an average of 408 mgs (cf. 332 mgs for Group 2). Importantly, when BIM-23014 was applied topically to the surgically traumatized area (left flank) rather than to the non-traumatized area (right flank) (Group 6), tumor growth was markedly inhibited resulting in tumors weighing 296 mgs, a Test/Control value of 72%.

Inhibition of trauma-induced growth of malignant melanoma

In one experiment, the effect of local surgical trauma on growth and responsiveness of cutaneous malignant melanoma (B16-F10) to BIM-23014 was studied. Under sterile precautions, a piece of full thickness skin, approximately 1 cm diameter, was excised from the right flank of syngeneic C57BL/6 conventional mice and wound immediately closed with Michel clamps on day 0. On day 1 all animals were implanted s.c. in the surgical area with B16-F10 cells. Treatment with BIM-23014 either on the side opposite from the tumor or intralesionally, was initiated on day 2.

Results of this experiment are summarized in Table 5 with data reported as means ±sem on 10 animal groups. Mean tumor weight in the non-surgically traumatized animals (Group 1) on day 15 was 765 mgs, whereas mean tumor weight in the surgically traumatized animals (Group 2) was 2280 mgs. Tumors implanted in the surgically traumatized area were almost three times larger (Test/Control value of 298%, p<0.001) than tumors in non-traumatized animals. Administration of BIM-23014 to non-surgically traumatized animals (Group 4) subcutaneously, distant from the tumor, had little tumor inhibitory effect inducing only a 90% Test/Control value (Group 4/Group 3). The same concentration of BIM-23014 administered intralesionally (surgical site) had a greater tumor inhibitory effect, inducing a 78% Test/Control value (Group 6/Group 5). The response to intralesional administration of BIM-23014 suggested the feasibility of applying BIM-23014 to the tumor or surgical site.

TABLE 5

Treatment of Surgical Trauma-Induced Proliferation (Malignant Melanoma)

| Group No. | Treatment | Tumor Weight Day 15* (mg) | Percent Test/ Control |
|---|---|---|---|
| 1 | No surgical trauma. Saline vehicle treated control, 0.2 ml/inj., s.c., b.i.d., q.d. 2–14. | 765 ± 40 | 298 |
| 2 | Surgical trauma day 0. Saline vehicle treated control, 0.2 ml/inj., s.c., b.i.d., q.d. 2–14. | 2280 ± 330 | |

TABLE 5-continued

Treatment of Surgical Trauma-Induced Proliferation (Malignant Melanoma)

| Group No. | Treatment | Tumor Weight Day 15* (mg) | Percent Test/ Control |
|---|---|---|---|
| 3 | No surgical trauma. 25% DMSO/saline vehicle treated control, 0.4 ml/inj., s.c., b.i.d., q.d 2–14. | 1034 ± 195 | 90 |
| 4 | No surgical trauma. BIM-23014, 600 µg/inj. in 25% DMSO/saline s.c., b.i.d., q.d. 2–14. | 928 ± 167 | |
| 5 | Surgical trauma. Saline vehicle treated control, 0.2 ml/inj., s.c., intralesional, b.i.d., q.d. 2–14. | 2039 ± 373 | 78 |
| 6 | Surgical trauma. BIM-23014, 500 µg/inj., s.c., intralesional, b.i.d., q.d. 2–14. | 1581 ± 311 | |

*Data presented as means ± s.e.m. on 10 animals/group. Significance of difference: Group 1 and Group 2 = p< 0.001; Group 2 and Group 4 = p < 0.05.

The following study was designed to demonstrate the therapeutic effect of applying BIM-23014 topically, either to the tumor site or to the surgically traumatized site, for inhibiting the proliferative surge of malignant melanoma following surgical trauma. The results, as well as a brief description of the experiment, are presented in Table 6 below. Data are reported as means ±s.e.m. on 8 animals/group. Syngeneic C57BL/6 conventional mice were used.

TABLE 6

Treatment of Surgical Trauma-Induced Proliferation (Malignant Melanoma)

| Group No. | Treatment | Tumor Weight Day 12* (mgs) | Percent Test/ Control |
|---|---|---|---|
| 1 | Melanoma Implanted, right flank day 0. No surgery, untreated shelf control. | 339 ± 60 | 212 |
| 2 | Surgically treated, melanoma implanted, right flank, day 0. Untreated shelf control. | 719 ± 134 | |
| 3 | Surgically treated, melanoma implanted, right flank, day 0. Placebo treated control, 0.05 ml 50% DMSO/saline vehicle, topical, b.i.d., q.d. 1–11. | 593 ± 214 | 89 |
| 4 | Surgically treated, melanoma implanted, tight flank, day 0. BIM-23014 treated, 0.05 ml 50% DMSO/saline containing 10 mg/ml BIM-23014, topical, b.i.d., q.d. 1–11. | 527 ± 117 | |
| 5 | Surgically treated left flank, melanoma implanted right flank, day 0. Surgical area treated placebo control, 0.05 ml 50% DMSO/saline vehicle, topical, b.i.d., q.d. 1–11. | 856 ± 248 | 57 |
| 6 | Surgically treated left flank, melanoma implanted right flank, day 0. Surgical area treated with BIM-23014, 0.05 ml 50% DMSO/saline vehicle containing 10 mg/ml | 488 ± 187 | |

TABLE 6-continued

Treatment of Surgical Trauma-Induced Proliferation (Malignant Melanoma)

| Group No. | Treatment | Tumor Weight Day 12* (mgs) | Percent Test/ Control |
|---|---|---|---|
| | BIM-23014, topical, b.i.d., q.d. 1–11. | | |

*Data presented as means ± s.e.m. on 8 animals/group. Significance of difference: Group 1 and Group 2 = p < 0.05.

More specifically, under sterile precautions, a piece of skin (full thickness) approximately 1 cm diameter was excised from the right flank of Groups 2, 3 and 4, and from the left flank of Groups 5 and 6. The wound was immediately closed with Michel clamps. The surgical procedure was carried out early in the a.m. of day 0. In the p.m. of the same day, $10^5$ B16-F10 melanoma cells were implanted, via syringe and needle, directly into the surgically treated (wound) area of Group 2, 3, and 4 and on the opposite, non-surgically treated right flank of Groups 1, 5 and 6.

Topical treatment with BIM-23014 (10 mg/ml in 50% DMSO/saline vehicle) and placebo (50% DMSO/saline) was initiated on day 1. Topical application was applied gently over and around surgical area. For Groups 5 and 6 animals, only surgical areas on the left flank were treated.

As shown in Table 6, malignant melanoma cells implanted s.c. in non-surgically traumatized animals on day 0 produced tumors with a mean weight of 339 mgs on day 12 (Group 1). The same size inoculum of melanoma cells, implanted directly into the traumatized area, produced tumors weighing 719 mgs in the same time period (Group 2), a trauma induced proliferative increase of over two times (Test/Control value of 212%, p<0.05). BIM-23014 applied directly to the tumor site resulted in tumors weighing 527 mgs (Group 4); whereas the 50% DMSO/saline placebo applied directly to the tumor site resulted in tumors weighing 593 mgs (Group 3), producing a Test/Control value of only 89%.

When the 50% DMSO/saline vehicle was applied to the surgically traumatized area on the left flank of animals bearing a tumor in the non-traumatized right flank (Group 5), there was no inhibitory effect with the tumors growing to an average of 856 mgs (cf. 719 mgs for Group 2). Importantly, when BIM-23014 was applied topically to the surgically traumatized area (left flank) rather than to the non-traumatized area (right flank) (Group 6), tumor growth was markedly inhibited resulting in tumors weighing 488 mgs, a Test/Control value of 57%.

OTHER EMBODIMENTS

The foregoing description has been limited to specific embodiments of this invention. It will be apparent, however, that variations and modifications may be made to the invention, with the attainment of some or all of the advantages of the invention. Such embodiments are also within the scope of the following claims.

What is claimed is:

1. A method for inhibiting in a mammal the accelerated growth of a solid primary or metastatic tumor resulting from tissue trauma caused surgically, non-surgically, or by tissue ulceration, said method comprising the step of administering to the site of said trauma in said mammal an amount of somatostatin or a somatostatin agonist after said trauma is induced, said amount being effective to inhibit said accelerated tumor growth.

2. The method of claim 1, wherein said tumor growth is caused surgically.

3. The method of claim 2, wherein said administering step is performed topically.

4. The method of claim 2, wherein said administering step is performed subcutaneously.

5. The method of claim 2, wherein said method comprises the step of administering to said mammal a therapeutically effective amount of a somatostatin agonist.

6. The method of claim 2, wherein said tumor is epithelial tumor.

7. The method of claim 6, wherein said tumor is prostate tumor, breast tumor, lung tumor, colon tumor, or melanoma.

8. The method of claim 7, wherein said tumor is prostate tumor, breast tumor, or melanoma.

9. The method of claim 5, wherein said tumor is epithelial tumor.

10. The method of claim 9, wherein said tumor is prostate tumor, breast tumor, lung tumor, colon tumor, or melanoma.

11. The method of claim 10, wherein said tumor is prostate tumor, breast tumor, or melanoma.

12. The method of claim 1, wherein said administering step is performed topically.

13. The method of claim 1, wherein said administering step is performed subcutaneously.

14. The method of claim 1, wherein said method comprises the step of administering to said mammal a therapeutically effective amount of a somatostatin agonist.

15. The method of claim 1, wherein said tumor is epithelial tumor.

16. The method of claim 15, wherein said tumor is prostate tumor, breast tumor, lung tumor, colon tumor, or melanoma.

17. The method of claim 16, wherein said tumor is prostate tumor, breast tumor, or melanoma.

18. The method of claim 14, wherein said tumor is epithelial tumor.

19. The method of claim 18, wherein said tumor is prostate tumor, breast tumor, lung tumor, colon tumor, or melanoma.

20. The method of claim 19, wherein said tumor is prostate tumor, breast tumor, or melanoma.

* * * * *